(12) United States Patent
Lang et al.

(10) Patent No.: US 9,962,113 B2
(45) Date of Patent: May 8, 2018

(54) SENSOR FOR MEASURING THE ACTIVITY OF BETA-PANCREATIC CELLS OR OF ISLETS OF LANGERHANS, MANUFACTURE AND USE OF SUCH A SENSOR

(75) Inventors: Jochen Lang, Bordeaux (FR); Bogdan Catargi, Bordeaux (FR); Sylvie Renaud, Pessac (FR); Matthieu Raoux, Bordeaux (FR); Gilles Charpentier, Merignac (FR)

(73) Assignees: UNIVERSITE DE BORDEAUX 1, Talence (FR); INSTITUTE POLYTECHNIQUE DE BORDEAUX, Talence (FR); CENTRE NATIONAL DE LA RECHERCHE SCIENTIFIQUE (CNRS), Paris (FR); UNIVERSITE BORDEAUX SEAGALEN, Bordeaux (FR)

( * ) Notice: Subject to any disclaimer, the term of this patent is extended or adjusted under 35 U.S.C. 154(b) by 563 days.

(21) Appl. No.: 13/521,724

(22) PCT Filed: Jan. 12, 2011

(86) PCT No.: PCT/EP2011/050359
§ 371 (c)(1),
(2), (4) Date: Oct. 4, 2012

(87) PCT Pub. No.: WO2011/086105
PCT Pub. Date: Jul. 21, 2011

(65) Prior Publication Data
US 2013/0030271 A1    Jan. 31, 2013

(30) Foreign Application Priority Data
Jan. 13, 2010 (FR) ...................... 10 50202

(51) Int. Cl.
*A61B 5/04* (2006.01)
*A61M 5/172* (2006.01)
(Continued)

(52) U.S. Cl.
CPC .......... *A61B 5/14532* (2013.01); *A61B 5/685* (2013.01); *A61M 5/1723* (2013.01);
(Continued)

(58) Field of Classification Search
CPC ........... A61B 5/425; A61B 5/04; A61B 5/145; A61B 5/14503; A61B 5/14532;
(Continued)

(56) References Cited

U.S. PATENT DOCUMENTS 3,827,565 A * 8/1974 Matsumura ................... 210/632
4,475,901 A * 10/1984 Kraegen et al. ................ 604/67
(Continued)

FOREIGN PATENT DOCUMENTS

| CN | 1856338 A | 11/2004 |
|---|---|---|
| CN | 1617753 A | 5/2005 |

(Continued)

OTHER PUBLICATIONS

Jobling, et al. "Active microelectrode array to record from the mammalian central nervous system in vitro" Med. & Biol. Eng. & Comput. 19 pp. 553-560 (1981).*
(Continued)

*Primary Examiner* — Lee S Cohen
*Assistant Examiner* — Erin M Cardinal
(74) *Attorney, Agent, or Firm* — Womble Bond Dickinson (US) LLP

(57) ABSTRACT

The invention relates to a sensor (2) including: a microelectrode assembly (21); and β-pancreatic cells (23) or islets (230) of Langerhans in culture on the microelectrode assembly (21); characterized in that the microelectrode assembly
(Continued)

(21) is designed to measure dynamically, continuously and in real time, electrical signals (V) produced by the β-pancreatic cells (23) or the islets of Langerhans (230) upon physiological activation. The invention also relates to the field of devices that can be implantable in the body of a patient, and including an insulin dispenser for dispensing an amount of insulin. The invention also relates to a method for manufacturing such a sensor and to such a device and a use of such a sensor.

16 Claims, 5 Drawing Sheets

(51) Int. Cl.
*A61B 5/145* (2006.01)
*A61B 5/00* (2006.01)
*A61M 5/142* (2006.01)

(52) U.S. Cl.
CPC ............ *A61B 5/425* (2013.01); *A61B 5/6848* (2013.01); *A61B 2562/028* (2013.01); *A61B 2562/0209* (2013.01); *A61B 2562/125* (2013.01); *A61M 5/14244* (2013.01); *A61M 5/14276* (2013.01); *A61M 2005/1726* (2013.01); *A61M 2230/201* (2013.01)

(58) Field of Classification Search
CPC . A61B 5/1473; A61B 5/14865; A61B 5/4845; A61B 5/6848; A61B 5/685; A61B 5/6876; A61B 2562/028; A61B 2562/046; A61B 2562/0209; A61B 2562/125; A61M 5/1723; A61M 5/14276; A61M 5/14244; A61M 2230/201
See application file for complete search history.

(56) References Cited

U.S. PATENT DOCUMENTS

| | | | |
|---|---|---|---|
| 4,633,878 A * | 1/1987 | Bombardieri | 600/347 |
| 5,050,612 A * | 9/1991 | Matsumura | 600/483 |
| 5,116,494 A * | 5/1992 | Chick | A61F 2/022 |
| | | | 210/192 |
| 6,605,039 B2 | 8/2003 | Houben et al. | |
| 2002/0038083 A1* | 3/2002 | Houben et al. | 600/365 |
| 2006/0057771 A1 | 3/2006 | Kovacs et al. | |
| 2008/0034972 A1* | 2/2008 | Gough et al. | 96/4 |
| 2009/0024017 A1* | 1/2009 | Ruffini | A61B 5/0408 |
| | | | 600/395 |
| 2009/0076340 A1* | 3/2009 | Libbus | A61B 5/0006 |
| | | | 600/301 |
| 2010/0202966 A1* | 8/2010 | Gross et al. | 424/9.1 |

FOREIGN PATENT DOCUMENTS

| | | |
|---|---|---|
| CN | 1973768 A | 6/2007 |
| DE | 39 41 873 A1 | 6/1991 |
| DE | 40 02 559 A1 | 10/1991 |

OTHER PUBLICATIONS

Guiseppi-Elie "Cleaning and Surface Activation of Microfabricated Interdigitated Microsensor Electrodes (IMEs), Planar Metal Electrodes (PMEs), Independently Addressable Microband Electrodes (IAMEs), and E'Chem 'Cell-On-A-Chip'" ABTECH Scientific (2000).*

Bornat, Y., et al., "Detection of Electrical Activity of Pancreatic Beta-Cells Using Micro-Electrode Arrays," *Fifth IEEE International Symposium on Electronic Design, Test & Applications*, Jan. 13-15, 2010, Ho Chi Minh City, Vietnam, XP002586590, pp. 233-236.

Office Action from Israeli Patent Application No. 220923, dated Feb. 2, 2014 (2 pages).

Office Action from Japanese Patent Application No. 2012-548425, dated Oct. 30, 2014 (2 pages).

* cited by examiner

SENSOR FOR MEASURING THE ACTIVITY OF BETA-PANCREATIC CELLS OR OF ISLETS OF LANGERHANS, MANUFACTURE AND USE OF SUCH A SENSOR

This is a non-provisional application claiming the benefit of International Application Number PCT/EP2011/050359 filed Jan. 12, 2011.

FIELD OF THE INVENTION

The invention relates to the field of sensors for a use, in particular but not limited to, in a diabetes treatment by insulin dispensing.

The invention also relates to the field of devices capable of being implanted in the body of a patient, and including an insulin dispenser for dispensing an amount of insulin.

The invention also relates to a process for producing such a sensor and such a device and a use of such a sensor.

PRIOR ART

Diabetes mellitus is caused by an excessively high blood glucose level (glycemia). This means that the patient's body is unable to metabolize glucose.

The metabolism of glucose is insulin dependent, a hormone secreted by β-pancreatic cells of the islets of Langerhans in the pancreas.

In some patients with diabetes mellitus, the β-pancreatic cells are either destroyed or insufficient, and there is no longer insulin secretion or secretion in a sufficient quantity (called "type-1" diabetes). In the context of so-called "type-1" diabetes, the treatment generally consists of injecting doses of insulin into the patient's body, sometimes several times per day, and monitoring the patient's diet.

A limited number of people with another type of diabetes mellitus called "type-2" (the patient's cells designed to capture and use glucose by means of insulin become insensitive to insulin) also use insulin injections.

In addition to insulin injections, it is also necessary to monitor the patient's blood glucose level several times per day so as to verify that the patient is not in a state of hypoglycemia, which is detrimental to the patient's health.

In addition, the insulin needs are dependent on the physical and intellectual state and activity of the person and are regulated by hormones.

To determine glycemia, the following is generally performed.

A finger of the patient is pricked by a needle and pressed so as to form a drop of blood. A tab connected to a device designed to determine glycemia is applied to the blood drop. The device indicates, generally on an LCD screen, the patient's blood glucose level (glycemia). This operation is therefore cumbersome.

For this reason, a less restrictive solution has been sought to enable glycemia to be monitored and ensure an insulin injection rate that is better suited to the patient's needs.

Recent developments have enabled continuous glycemia monitoring.

One solution consists of introducing electrochemical sensors into the patient's body, including electrodes linked to an enzyme, glucose oxidase. Glucose oxidase reacts, in the presence of oxygen, with the glucose present in the blood so as to produce oxygenated water and gluconolactone. The oxygenated water is then oxidized and transformed into water by the electrodes, which then produce an electrical current proportional to the blood glucose concentration.

The major disadvantage of this solution is that it does not enable information on insulin needs to be collected, because of the technology used, which detects only glycemia but not other hormonal regulators or glucose metabolism, and does not take into account the glucose homeostasis, i.e. the body's ability to maintain a glycemic balance enabling it to function in spite of external constraints tending to move the body away from this balance. Moreover, the information cannot be collected in real time.

Non-invasive solutions exist, such as:
surface-enhanced Raman spectroscopy;
fluorescence spectroscopy;
reverse iontophoresis;
photoacoustic spectroscopy;
thermal or impedance spectroscopy; or
electromagnetic field measurement.

However, these non-invasive solutions are not suitable for use outside of constant medical monitoring, for example a hospital environment.

All of the conventional solutions mentioned above use a single parameter, namely the blood glucose level, to determine the need for insulin and/or glucose, while other compounds such as other hormones, lipids and certain amino acids modulate the insulin and/or glucose needs physiologically. Thus, the blood glucose level does not always alone reflect the real need for insulin and/or glucose. For this reason, complex algorithms taking the physiological situation into account are necessary to overcome the use of a single parameter.

Moreover, such solutions produce less reliable results in the detection of hypoglycemic states that are dangerous for the patient's health.

Finally, they enable insulin to be dispensed in waves. The dispensing of insulin in waves would enable insulin resistance to be avoided, i.e. cases in which, in spite of the presence of insulin, the patient's body does not successfully metabolize the glucose.

Also, in the field of research on β-pancreatic cells, studies on new therapeutic principles or toxic agents are relatively complex and difficult for screening approaches. These studies may also require the use of gene therapy, which thus alters the native state of the β-pancreatic cells.

Presentation

The invention is therefore intended to overcome at least one of the disadvantages mentioned above.

The invention also relates to the long-term observation of the state of β-pancreatic cells or islets of Langerhans so as to elucidate the effect of substances on their electrical activity.

A sensor according to claim 1 is proposed by the invention.

One advantage of using β-pancreatic cells or islets of Langerhans is that the sensor can provide information closer to the patient's physiological state than the glucose sensors described above.

Another advantage is that such a sensor can also be used to study clonal β-pancreatic cells or primary β-pancreatic cells or ex-vivo islets, in particular for studying β-pancreatic cells or islets with a view to screening toxic molecules or molecules for therapeutic purposes.

Such a sensor also enables cells to be monitored during their differentiation from stem cells into β-pancreatic cells and optionally the structuring thereof into islets of Langerhans.

Other optional and non-limiting features of this sensor are covered in claims 2 to 10.

The invention relates to a device according to claim 11 or 12.

The invention also relates to a process for producing such a sensor and such a device, according to claim 13.

The invention also relates to a use of such a sensor, according to claim 14.

An advantage of using β-pancreatic cells or islets of Langerhans is that the sensor may provide information closer to the patient's physiological state than the glucose sensors described above.

PRESENTATION OF THE FIGURES

Additional features, objectives and advantages of the invention will appear in the following detailed description, in reference to the drawings provided for illustrative and non-limiting purposes, in which.

In all of the figures, similar elements are denoted by the same numeric references.

DETAILED DESCRIPTION

Sensor

A sensor 2 according to the invention is described below in reference to FIGS. 1 and 5 to 7.

The sensor 2 may be used in devices suitable for treatment of type-1 or type-2 diabetes, by dispensing insulin.

The sensor 2 includes primarily a set of microelectrodes 21; and β-pancreatic cells 23 or islets 230 of Langerhans, containing β-pancreatic cells 23, in culture on the set of microelectrodes 21.

The set of microelectrodes 21 is suitable for measuring, in real time and continuously, electrical signals V produced by the β-pancreatic cells 23 or islets 230 of Langerhans during their physiological activation.

Figure 1:
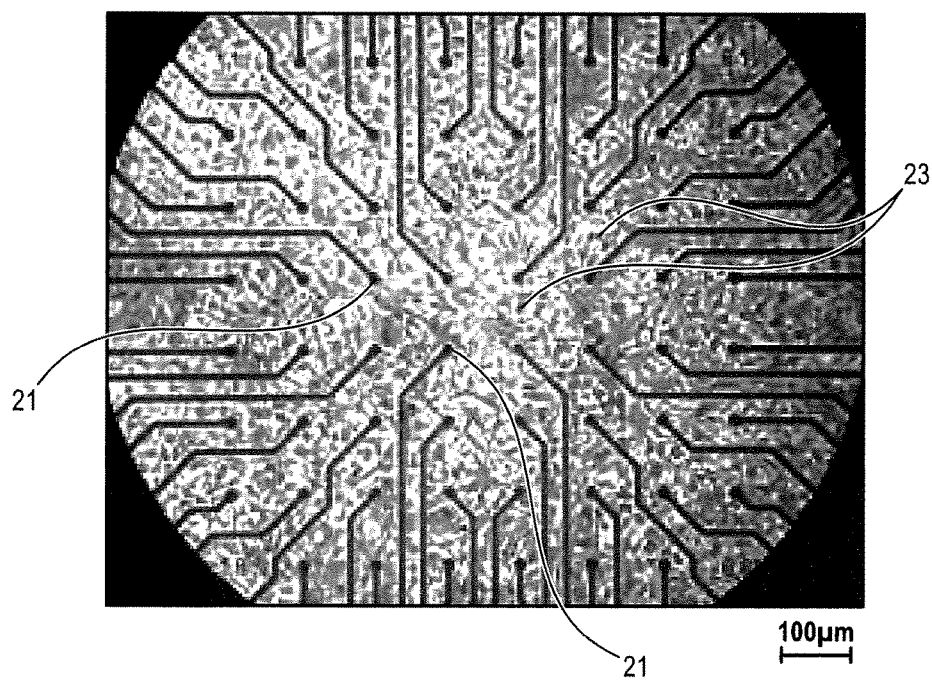
FIG. 1 is a partial illustration of the sensor, from a top view, at the level of the electrodes and β-pancreatic cells or islets of Langerhans.

As shown in FIG. 1, the distribution of the microelectrodes 21 over the sensor 2 is such that the microelectrodes 21 uniformly cover the sensor 2, according to a regular and conventional geometry. The microelectrodes 21 are spaced apart by a distance of between 50 and 200 μm. The set of microelectrodes 21 has a microelectrode density of between 20 and 200 microelectrodes per square millimeter.

In the example embodiment shown in FIG. 1, the sensor 2 includes a set of 60 microelectrodes distributed over 1 mm$^2$. The microelectrodes 21 have a disk shape 10 μm in diameter.

The sensor 2 also includes β-pancreatic cells 23 in culture on the set of 60 microelectrodes 21.

The sensor 2 is distinguished from the sensors used in conventional type-1 or type-2 diabetes treatment devices in that it does not measure only glycemia. Indeed, as specified above, the conventional sensors use gluconolactone to indirectly measure glucose, of which the level in the blood is assumed to reflect the patient's need for insulin, which is not necessarily correct, as seen above.

The use of β-pancreatic cells makes it possible to get closer to the natural biological functioning of the pancreas of a healthy individual, which is sought to be reproduced in an individual with type-1 or type-2 diabetes (patient). Indeed, the β-pancreatic cells regulate glycemia by secreting insulin. Their physiological activation produces electrical signals, for example electric potentials. Thus, the physiological activation of a β-pancreatic cells involves a dynamic variation in the electric potential on both sides of its membrane. This dynamic variation has a time-dependent amplitude profile called a waveform and that reflects the physiological behavior of the β-pancreatic cells and thus the patient's need for insulin. For example, there are specific profiles called action potentials known to a person skilled in the art and which correspond to a rapid and amplified variation in the electric potential beyond a potential threshold. These action potentials may be identified.

Figure 3:
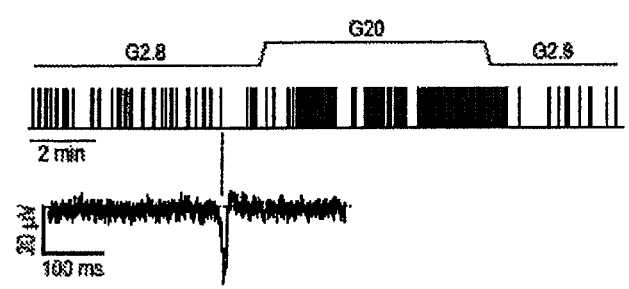
FIG. 3 is a graph showing the variation in the reaction of the β-pancreatic cells in the presence of glucose at two different concentrations.

In the case of β-pancreatic cells, the frequency of the action potentials increases with the secretion of insulin. As shown in FIG. 3, the electric potentials are measured, in real time and continuously, i.e. dynamically, on the millisecond scale.

The use of islets of Langerhans makes it possible to get even closer to natural biological functioning, since the β-pancreatic cells, representing two-thirds of the cells of the islets of Langerhans, are in their natural environment.

The use of β-pancreatic cells or islets of Langerhans enables information to be obtained on the patient's need for insulin, enabling the patient's glycemia to be regulated in a manner similar to the glycemia regulation in a healthy individual.

The sensor 2 may also include at least one set of processing units 25. Each microelectrode 21 is then coupled to a single processing unit 25 for forming the electrical signals V measured, and extracting at least one parameter P indicating a need for insulin.

The parameter P may also indicate the state of electrical activity of the β-pancreatic cells 23 or the islets 230 of Langerhans for physiological study. This physiological study may be performed in the context of screening toxic molecules or monitoring cells to study their differentiation from stem cells into β-pancreatic cells, i.e. their structuring into islets of Langerhans. This physiological study can also be performed for therapeutic ends.

The advantage of providing one processing unit 25 per microelectrode 21 is that it enables the continuous and real-time processing of the electrical signals V measured.

Preferably, the processing units 25 are customized analog microelectronic circuits, for example produced with submicronic CMOS technology. This microelectronic integration solution is optimal for obtaining a high circuit integration density (several mm2) and a low energy consumption, enabling longer duration of use of the sensor 2 and limiting the increase in temperature around the sensor 2. The analog processing of the signals indeed makes it possible to do without the presence of a digital calculation (on a standard or dedicated processor) and therefore minimizes the internal connections to the circuit by coding each signal on a single wire. In addition, the production of standard CMOS technology processing units 25 is inexpensive.

The processing unit 25 includes a sub-unit 251 and a sub-unit 253.

The formation of the signals is performed by the sub-unit 251, which receives the electrical signals V from the microelectrodes 21 and processes them according to amplification and/or filtering-type mathematical functions. In the case of measuring electric potentials, the sub-unit 251 may detect in particular the action potentials.

The extraction of the parameter P is performed by the extraction sub-unit 253; the value of the parameter P is calculated on the basis of input signals of the sub-unit 253 comprising the electrical signals V formed and a set-point value Vc. The set-point value Vc indicates a normal activation of the β-pancreatic cells 23 or the islets 230 of Langerhans.

The sensor 2 can also include a regulator 26 for transforming the parameter P indicating the need for insulin into a control signal C, to control an insulin dispenser 3. There is a regulator 26 for all of the processing units 25. The control signal C obtained is dependent on the difference between the parameter P extracted by the processing unit 25 and the set-point value Vc, as well as the derivative of this difference. In particular, the control signal C is dependent on the waveform of the electrical signals V formed—due to the temporal and statistical processing of the electrical signals V measured—and/or the frequency characteristics of the electrical signals V formed. The regulator 26 also takes into account safety set-points such as relative and absolute limits of the amount of insulin to be dispensed and/or a limitation of variations in the amount of insulin to be dispensed.

For example, the regulator 26 may implement a threshold detection variable according to the standard deviation of the electrical signal V formed or the frequency of the oscillations; wavelet filtering; etc.

The set of microelectrodes 21 and/or the set of processing units 25 and/or the regulator 26 may be produced or placed on a semiconductor material, for example silicon.

The set of microelectrodes 21 and/or the set of processing units 25 and/or the regulator 26 can be produced or placed on the same semiconductor substrate or on separate substrates, then electrically interconnected as a consequence (owing to metalized tracks M or flexible connections F).

Figure 5:
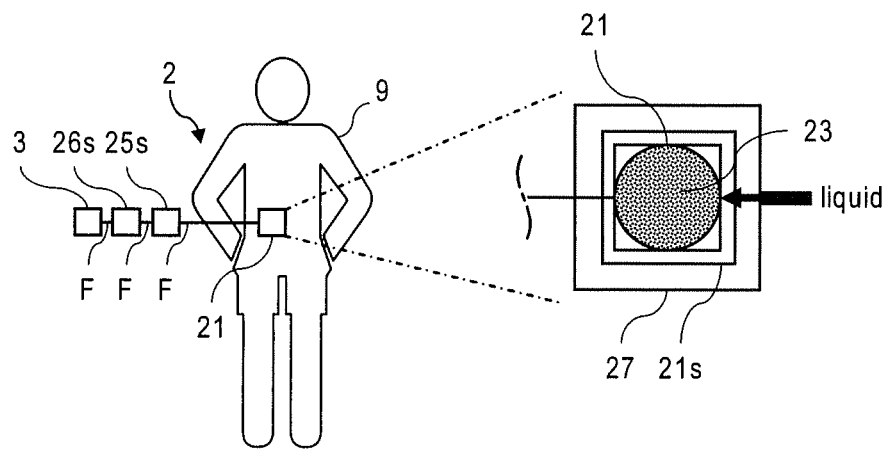
FIG. 5 is a diagram showing the insulin-dispensing device according to an embodiment of the invention.
Figure 6:
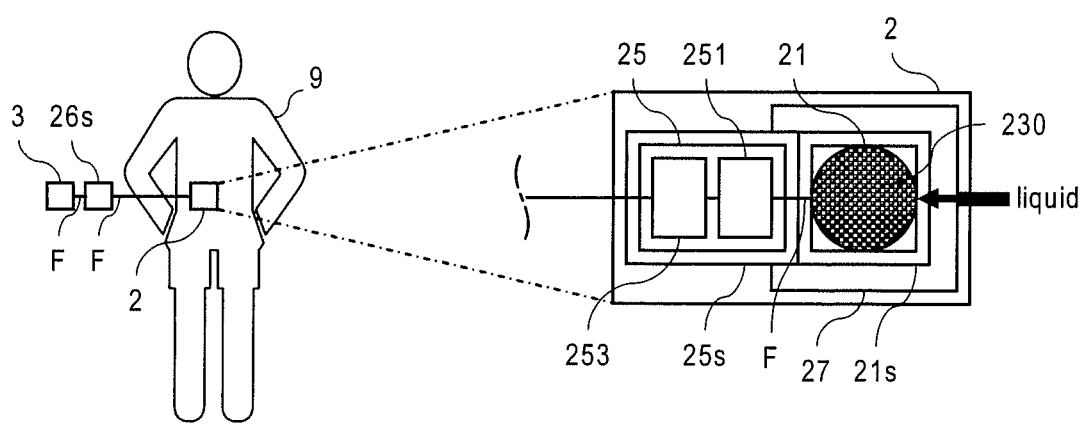
FIG. 6 is a diagram showing the insulin-dispensing device according to another embodiment of the invention.
Figure 7:
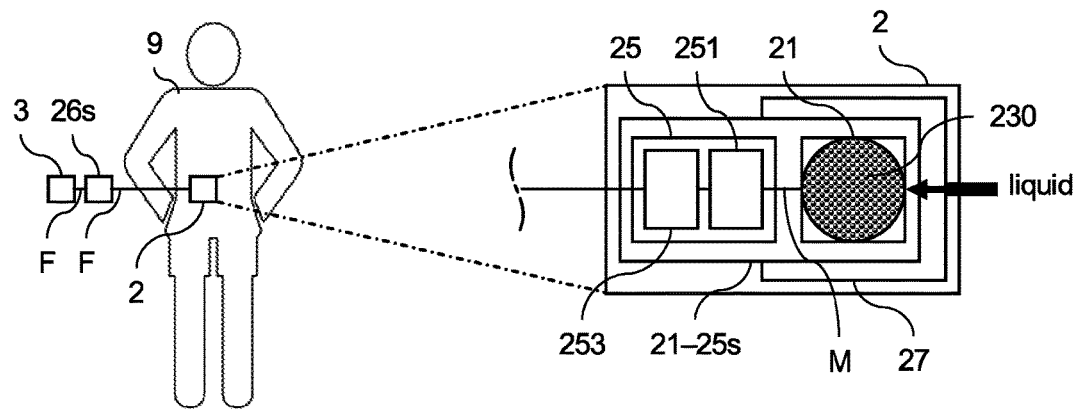
FIG. 7 is a diagram showing the insulin-dispensing device according to an embodiment of the invention.

For example, as shown in FIGS. 5 to 7, the set of microelectrodes 21, the set of processing units 25 and the regulator 26 are produced on separate silicon substrates 21s, 25s, 26s and connected by flexible connections F (see FIGS. 5 to 7). Optionally, the separate silicon substrates 21s, 25s, 26s may be placed on the same substrate 28, then electrically connected to one another in a manner known to a person skilled in the art (see FIG. 6).

In the example of FIG. 7, the set of microelectrodes 21 and the set of processing units 25 are produced directly on the same silicon substrate 21-25s and are electrically connected by metalized tracks M.

Figure 8:
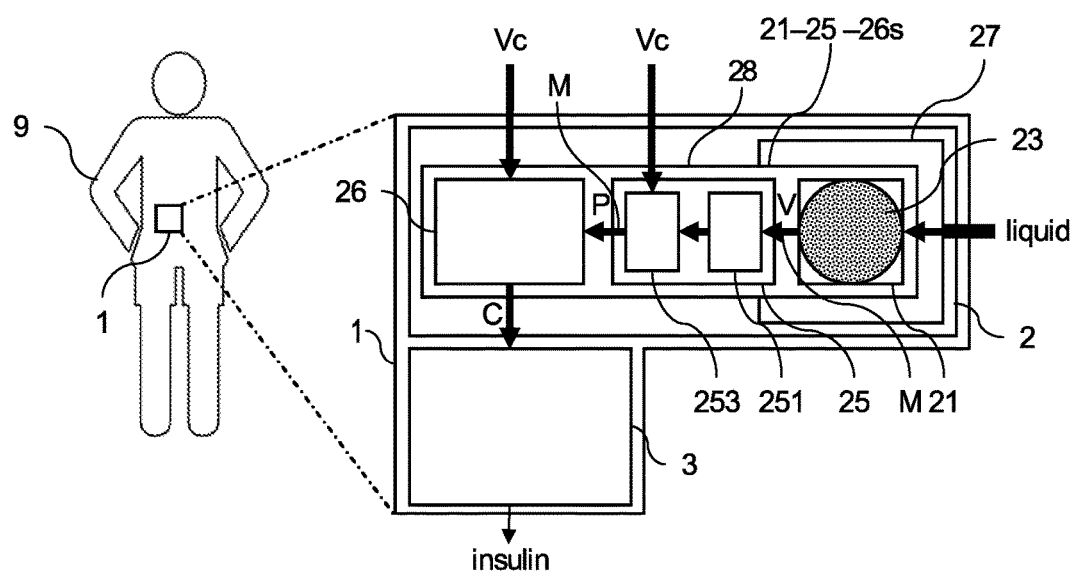
FIG. 8 is a diagram showing the insulin-dispensing device according to another embodiment of the invention.

In the example of FIG. 8, the set of microelectrodes 21, the set of processing units 25 and the regulator 26 are produced directly on the same silicon substrate 21-25-26s and electrically connected by metalized tracks M.

The advantage of producing the set of processing units 25 directly on the semiconductor substrate is that it avoids the degradation of the electrical signals V produced by the β-pancreatic cells 23 or the islets 230 of Langerhans and measured by the set of microelectrodes 21, and the loss of information associated with extracorporeal processing of the electrical signals V.

The production of the set of microelectrodes 21, the set of processing units 25 and the regulator 26 on the semiconductor substrates 21s, 23s, 25s, 21-25s, 21-25-26s is already known to a person skilled in the art and will not be described in greater detail below. An example of microelectrode array (MEA) technology will cited.

The sensor 2 can be adapted so as to be implanted at least partially in the body of a patient 9 as shown in FIGS. 5 to 8. If the sensor 2 is partially implantable in the patient's body 9, at least the set of microelectrodes 21 and the β-pancreatic cells 23 or islets 230 of Langerhans are inside the patient's body 9. Preferably, the set of processing units 25 is also inside the patient's body 9 (FIG. 7). It is also possible to produce a sensor 2 including a set of microelectrodes 21, β-pancreatic cells 23 or islets 230 of Langerhans, the set of processing units 25 and the regulator 26, and being entirely implantable in the patient's body 9 (FIG. 8).

The sensor 2 is preferably implanted in the interstitial tissue, near an artery or the peritoneum of patient's body 9.

The body's antibodies attack all molecules recognized as being foreign or not compatible with the immune system of the patient's body 9, as is the case for grafts.

To avoid this rejection, the sensor 2 may also include a semi-permeable membrane 27 suitable for filtering a liquid, for example blood, that must access the β-pancreatic cells 23 and block any molecule contained in the liquid of which the weight is greater than 65 kDa (kilodalton; 1 Da=$1.67 \cdot 10^4$ g). Thus, there is no need to choose β-pancreatic cells or islets of Langerhans that are compatible with the immune system of the patient 9: in the presence of the membrane 27, the risk of rejection is reduced and there is no need to prescribe immunosuppressants.

The electrical power supply of the sensor 2 may be internal or external. In the latter case, the power supply must be mobile and be capable of accompanying the patient 9 as he or she moves around. The external power supply may be produced by external induction. The internal power supply may be produced by battery.

The β-pancreatic cells 23 or islets 230 of Langerhans may be of porcine, murine (mice or rats, for example) or human origin. The β-pancreatic cells may also be of clonal origin (i.e. they have been cloned from one or more β-pancreatic cells) or obtained from stem cells (i.e. from cells not yet differentiated and capable of being transformed into any type of cell). The human β-pancreatic cells may also be cadaveric, i.e. come from donors before their physiological functions have been affected post mortem.

The quantity of β-pancreatic cells 23 on the microelectrodes 21 is between 0.01 and 1% of the quantity of β-pancreatic cells in the pancreas of a healthy individual. Preferably, the quantity of β-pancreatic cells 23 is 0.1% of the quantity of β-pancreatic cells in the pancreas of a healthy individual.

The number of islets 230 of Langerhans is determined so that the quantity of β-pancreatic cells contained in these islets 230 of Langerhans is between 0.01 and 1% of the quantity of β-pancreatic cells in the pancreas of a healthy individual. Preferably, the number of islets 230 of Langerhans is determined so that the quantity of β-pancreatic cells is 0.1% of the quantity of β-pancreatic cells in the pancreas of a healthy individual.

The sensor 2 may be used for purposes other than insulin therapy. Indeed, the sensor 2 may be used for various tests such as screening (test in which several hundred and even thousands of components are deposited on at least as many sensors) or laboratory analysis (extracorporeal measurement of need for glucose, for example).

Results Obtained

Laboratory tests have been conducted on the sensor 2 of FIG. 1.

Figure 2:
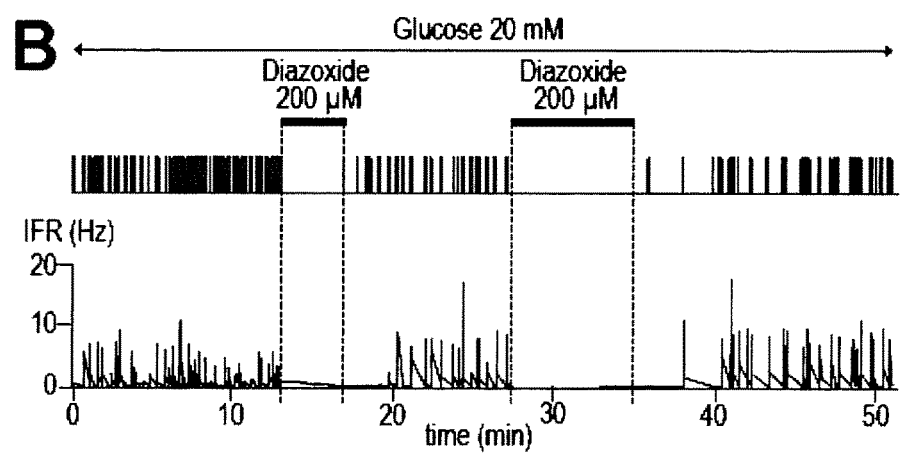
FIG. 2 is a graph showing the reaction of β-pancreatic cells in the presence of glucose, activating electrical signals, diazoxide, a pharmacological agent known for its glucose response inhibition at the level of the β-pancreatic cells or the islets of Langerhans.

FIG. 2 shows the activation of β-pancreatic cells 23 of the sensor 2 in the presence of glucose and diazoxide.

It is known that, in vivo, the presence of glucose leads to a production of electrical signals, for example, in the form of electric potentials of which the profile may have the form of action potentials in β-pancreatic cells of a healthy individual. The β-pancreatic cells then release insulin. It is also known that, in vivo, diazoxide inhibits the effect of glucose on the β-pancreatic cells of a healthy individual, i.e. in the combined presence of glucose and diazoxide, and the β-pancreatic cells do not produce an action potential and therefore do not secrete insulin.

The first line of FIG. 2 specifies the times at which glucose is present at 20 mM, i.e. from 0 to 50 min. The second line specifies the times at which diazoxide is present at 200 μM, i.e. from around 13 to 16 min and around 27 to 35 min. In the third line, each bar represents the occurrence of an action potential identified in the electrical signal V. The fourth line shows the instantaneous frequency of these action potentials (IFR in hertz) as a function of time (in minutes).

It is possible to see that the β-pancreatic cells of the sensor 2 have a sustained physiological activity in the presence of glucose without diazoxide, while, in the presence of diazoxide, the β-pancreatic cells 23 of the sensor 2 have a basal physiological activity (activation of zero β-pancreatic cells 23).

It is also possible to see that the effect of diazoxide is not definitive. Indeed, when there is no more diazoxide, the electrical activation of the β-pancreatic cells 23 of the sensor 2 becomes sustained again in the presence of glucose alone.

The β-pancreatic cells 23 of the sensor 2 therefore have a physiological behavior with respect to diazoxide.

FIG. 3 shows the variation in the occurrence of action potentials identified in the electrical signal V measured on the β-pancreatic cells 23, as a function of the glucose concentration. The first line shows the glucose concentration. In the second line, each bar shows the occurrence of an action potential. The fourth line shows the electrical signal V as measured dynamically in analog form and continuously. An action potential waveform is visible at the dotted vertical line.

It can be seen in FIG. 3 that the occurrence of action potentials in the electrical signal V is higher when the glucose concentration is 20 mM than when the glucose concentration is 2.8 mM.

The electrical activity of the β-pancreatic cells 23 therefore varies with the glucose concentration and the occurrence of action potentials increases with it, corresponding to what happens for β-pancreatic cells of the pancreas of a healthy individual.

Figure 4:
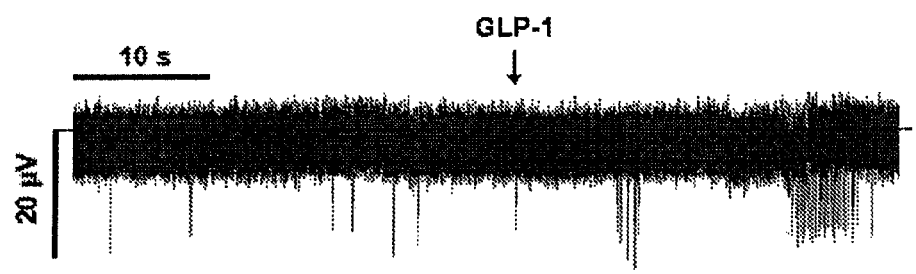
FIG. 4 is a graph showing the reaction of β-pancreatic cells in the presence of the incretin hormone GLP-1, a physiological amplifier of the glucose response.

FIG. 4 shows the influence of an incretin hormone, GLP-1, on the production of action potentials in β-pancreatic cells 23 of the sensor 2. It is known that, for a healthy individual, the incretin hormone GLP-1 increases the production of action potentials in β-pancreatic cells and therefore the secretion of insulin.

The first line of FIG. 4 specifies the time at which the β-pancreatic cells 23 of the sensor 2 are placed in contact with the incretin hormone GLP-1, shown by a vertical arrow.

The second line shows the electrical signal V measured dynamically in real time and continuously, with the occurrences of action potentials that can be seen in the form of downward peaks.

It can be seen that the electrical activation of the β-pancreatic cells 23 of the sensor 2 increases significantly some twenty seconds after injection of the incretin hormone GLP-1. This clearly reproduces what is observed in the natural environment of β-pancreatic cells of the pancreas of a healthy individual.

Method for Producing a Sensor

Figure 9:
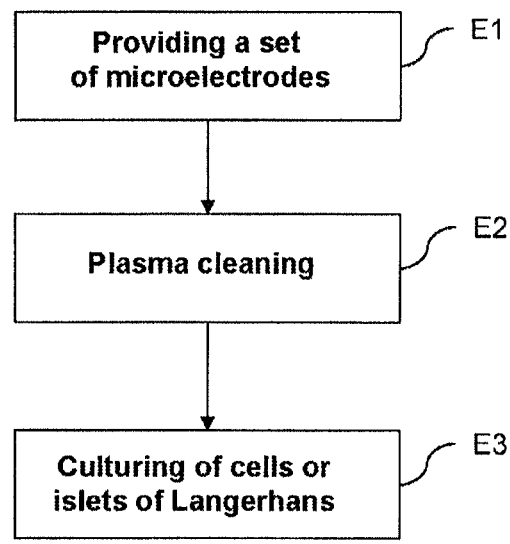
FIG. 9 is a flow chart showing an example of the implementation of the sensor production process.

In reference to FIG. 9, a method for producing the above-described sensor 2 is described.

This method includes the following steps:
- providing E1 with a substrate 21*s*, 21-25*s*, 21-25-26*s* having a set of microelectrodes 21, optionally a set of processing units 25 and/or a regulator 26;
- cleaning E2 of the substrate 21*s*, 21-25*s*, 21-25-26*s* by plasma; and
- culture E3 of β-pancreatic cells 23 or islets 230 of Langerhans on the set of microelectrodes 21.

The cleaning E2 of the substrate with plasma ("plasma cleaner") enables the surface of the substrate 21*s*, 21-25*s*, 21-25-26*s* to be made hydrophobic and prepares it for the adhesion of the β-pancreatic cells 23 on the substrate 21*s*, 21-25*s*, 21-25-26*s*.

The β-pancreatic cells 23 or islets 230 of Langerhans are obtained in a conventional manner.

Insulin Dispensing Device

An example of a possible device 1 for dispensing insulin is described below in reference to FIGS. 5 to 8.

This device 1 includes an insulin dispenser 3 for dispensing an amount of insulin into the body of a patient 9.

The device 1 also includes a sensor 2 as described above.

The insulin dispenser 3 can be implantable in the patient's body 9. This is not obligatory, as the insulin dispenser 3 may also be outside the patient's body 9.

If the insulin dispenser 3 and the sensor 2 are entirely implantable in the patient's body 9, the patient 9 will not be disturbed by the presence of an external object connected to his or her body. In addition, this is aesthetically and psychologically advantageous. The power supply of the device 1 may be the same as that of the sensor 2.

The glycemia regulation is performed by means of this device 2 in a closed loop. Indeed, the β-pancreatic cells 23 produce electrical signals V as a function of the patient's 9 need for insulin, the set of microelectrodes 21 measures these electrical signals V and the set of processing units 25 forms them and extracts the parameter P therefrom. This parameter P is received by the regulator 26 that, on the basis of this parameter P, generates and sends a control signal C to the insulin dispenser 3. The insulin dispenser 3 dispenses the amount of insulin corresponding to the control signal C. The insulin dispensed acts on the glycemia and thus modifies the patient's 9 subsequent need for insulin and the reduction in glycemia leads to a reduction in the activation of the β-pancreatic cells with a reduction in the frequency of the action potentials, and therefore the return to the baseline and the stopping of the control signal C until there is another increase in glycemia, for example during a meal.

The invention claimed is:

1. A sensor including:
   microelectrodes which are configured to dynamically measure in real time and continuously, electrical signals produced by all cells types in islets of Langerhans in culture disposed on the microelectrodes during their physiological activation, wherein the sensor also includes at least one set of processing units, in which each processing unit is coupled to a corresponding one of said microelectrodes and:

each processing unit is configured to process the electrical signals measured by said corresponding one of said microelectrodes and extract at least one parameter from said processed electrical signals indicating a need for insulin by a patient, in real time and continuously.

2. The sensor of claim 1, in which at least one of the processing units is configured to detect action potentials in the electrical signals.

3. The sensor of claim 1, also including a regulator for transforming the parameter indicating the need for insulin into a control signal for controlling an insulin dispenser.

4. The sensor of claim 1, also including a semiconductor substrate comprising at least the microelectrodes.

5. The sensor of claim 1, also including a semi-permeable membrane, for:

filtering a liquid needing access to the islets of Langerhans, and blocking the molecules of said liquid of which the weight is greater than 65 kDa.

6. The sensor of claim 5, configured to be implanted in the patient's body.

7. The sensor of claim 1, in which the islets of Langerhans are of porcine, murine or human origin.

8. The sensor of claim 1, in which each processing unit:

extracts at least one parameter indicating the state of electrical activity of the islets of Langerhans for:

a physiological study for screening toxic molecules; or a physiological study for a therapeutic end; or a physiological study for monitoring the differentiation of cells from stem cells into β-pancreatic cells.

9. The sensor of claim 1, wherein each said processing unit includes an action potentials detector sub-unit and an extraction sub-unit.

10. The sensor of claim 1, wherein the processing units are analog microelectronic units.

11. The sensor of claim 10 wherein the analog microelectronic units include sub-micronic CMOS technology.

12. The sensor of claim 1, wherein the at least one parameter is calculated from the processed electrical signals and a set-point value.

13. A device including an insulin dispenser for dispensing an amount of insulin into the patient's body, and the sensor of claim 1, wherein the sensor is configured to control the insulin dispenser.

14. The device of claim 13, which is configured to be implantable into the patient's body.

15. A process for producing the sensor of claim 1, including:

providing a substrate having the microelectrodes and the processing units, cleaning the substrate with plasma;

culturing islets of Langerhans on the microelectrodes.

16. The sensor according to claim 1, wherein each said processing unit is configured for processing the electrical signals according to mathematical functions of at least one of amplification and filtration.

* * * * *